United States Patent
Masuda

(10) Patent No.: US 7,475,438 B2
(45) Date of Patent: Jan. 13, 2009

(54) PORTABLE BIDET

(75) Inventor: Tomoe Masuda, Tokyo (JP)

(73) Assignee: WBE Co., Ltd., Tokyo (JP)

( * ) Notice: Subject to any disclaimer, the term of this patent is extended or adjusted under 35 U.S.C. 154(b) by 491 days.

(21) Appl. No.: 10/550,872

(22) PCT Filed: Aug. 13, 2003

(86) PCT No.: PCT/JP03/10318

§ 371 (c)(1), (2), (4) Date: Sep. 27, 2005

(87) PCT Pub. No.: WO2005/002410

PCT Pub. Date: Jan. 13, 2005

(65) Prior Publication Data

US 2007/0000041 A1    Jan. 4, 2007

(30) Foreign Application Priority Data

Jul. 8, 2003    (JP)    ............... 2003-193584

(51) Int. Cl.
*A47K 3/022*    (2006.01)
(52) U.S. Cl. .......................................... 4/443; 604/212
(58) Field of Classification Search ............... 4/443; 604/197, 212, 911
See application file for complete search history.

(56) References Cited

U.S. PATENT DOCUMENTS

| | | | | | |
|---|---|---|---|---|---|
| 268,805 | A | * | 12/1882 | Knight | 604/217 |
| 1,923,409 | A | * | 8/1933 | Ziegler | 604/212 |
| 2,180,063 | A | * | 11/1939 | McKinley | 604/33 |
| 3,635,218 | A | * | 1/1972 | Ericson | 604/37 |
| 3,892,311 | A | * | 7/1975 | Sneider | 206/229 |
| 5,428,303 | A | * | 6/1995 | Pasqualini | 326/27 |

FOREIGN PATENT DOCUMENTS

| | | |
|---|---|---|
| EP | 0 985 400 | 3/2000 |
| JP | 7-45004 | 12/1995 |
| JP | 9-192197 | 7/1997 |
| JP | 2000-139760 | 5/2000 |

* cited by examiner

*Primary Examiner*—Charles E Phillips
(74) *Attorney, Agent, or Firm*—Wenderoth, Lind & Ponack, L.L.P.

(57) ABSTRACT

A portable bidet includes a cylindrical member for storing washing liquid, and an airbag section connected to the cylindrical member for supplying air upon squeezing to cause injection of washing liquid. The cylindrical member is formed of hard resin and has an arcuate tip end portion and at least one ejection port. An extruding member is disposed in the cylindrical member. The ejection port is closed by a releasable film member after the washing liquid is stored. The airbag section is formed of flexible or soft resin having a sealable air inlet, and when not in use, can be collapsed and packed alongside the cylindrical member.

4 Claims, 3 Drawing Sheets

PORTABLE BIDET

TECHNICAL FIELD

The present invention relates to a portable bidet that can be packaged compactly and hence is regularly portable, and can be used immediately and quickly without any troublesome operation for washing, sterilization, disinfection, and odor elimination of the private parts when desired.

BACKGROUND ART

Hitherto, the portable bidet of this type is required, for example, to be capable of using in a toilet without provision of a bidet and to be convenient for carry, consequently those of various configurations have been developed and known.

In these circumstances, for example, there is publicly known "Portable bidet" which comprises a flexible water storage bag of synthetic resin film, a water tube mounted to the water storage bag and acting as a water passage, a spray nozzle mounted to a tip end of the water tube, and a valve assembly interposed between the spray nozzle and the water tube, wherein the water tube located in the water storage bag is fusion bonded by heat to an inner surface of the water storage bag, and the spray nozzle is formed with an injection hole for causing water to inject sideway at a tip end portion, or with a projecting wall formed near the tip end portion thereof (JP-A-2000-139760 (Prior Art Document 1), see pages 2 to 6 and FIG. 1).

In this arrangement, the entire device can be compactly folded and carried by emptying the water storage bag, and when in use, the spray nozzle and the valve assembly are taken out from the water tube, a required quantity of water such as tap water is stored in the water storage bag from the opened water tube, and then the valve assembly is arranged at the opening of the water tube, and the spray nozzle is screwed in, so that inside water is fed from the water tube via the valve assembly to the spray nozzle by squeezing and hence pressurizing the water storage bag to cause water to be injected from a nozzle head.

Also, there is publicly known a structure for making it convenient to carry about, for example, and which comprises a resilient washing liquid case to store washing liquid such as distilled water and having an opening covered by a lid member, a washing tube provided so as to be capable of projecting and retracting through an insertion port provided at a center of the lid member, and a valve body provided on the rear end side of the washing tube by forming the distal side of the washing tube larger in diameter so that the insertion port is closed when the washing tube is retracted and a washing liquid inflow port is opened when the washing tube is pulled out, whereby a complex structure for opening the valve body and a structure for fixedly maintaining the pulled washing tube are formed at an inside of the lid member and the rear end side of the washing tube (JP-U-7-45004 (Prior Art Document 2), see pages 1-2 and FIGS. 1, 2).

In this arrangement, the washing tube assumes a state of being retracted in the washing liquid case when it is carried, and hence it conveniently does not require much space and, when in use, the washing tube is pulled out and the washing liquid inflow port of the valve body is opened, so that washing water is spouted out from the tip end of the washing tube by squeezing the washing liquid case.

However, although the invention disclosed in the above-described Prior Art Document 1 is convenient because it can be carried in a state in which washing water is not filled in the water storage bag, when the valve assembly and the spray nozzle are attached to the opening of the water tube after having removed the spray nozzle and the valve assembly from the water tube and having filled water such as tap water in the water storage bag for use, if the valve assembly is attached in the wrong direction, water cannot be injected even though the water storage bag is strongly squeezed, and hence it is necessary to remove them and attach again. Therefore, such attaching and detaching operation is troublesome, and not only usage of unsterilized tap water is a point of anxiety, but also pain or discomfort may result when it is inserted into the private part if the nozzle head is projected sideway or the projecting wall is provided near the tip end portion. Furthermore, there is a disadvantage that contaminated water that flows out from the private part after washing may wet (contaminate) the hand.

In the invention disclosed in the above-described Prior Art Document 2, since washing liquid is filled in the case in advance, it causes no anxiety from a point that usage of unsterilized water such as tap water is avoided. However, when the washing tube is pulled out with excessive force for use, the washing tube may be detached. In contrast, if it is pulled insufficiently, the washing liquid inflow port of the valve body may not be opened sufficiently. Therefore, the pulling stroke and degree of opening of the washing liquid inflow port of the valve body cannot be recognized, and hence it causes anxiety for the user. In addition, there is a disadvantage in terms of structure, in that contaminated water that flows out from the private part after washing may wet (contaminate) the hand when in use, and in that the structure of the lid member, the structure of the washing tube, and the structure of the valve body are complicated, and hence the number of components increases and the cost may increase.

Therefore, the portable bidet in the related art has problems to be solved in order to make it easy to carry without taking up much space as a matter of course, but also to achieve easy operation during use, to eliminate various inconveniences during use, to reduce the number of components to simplify and reduce the cost, and to achieve sterilization, disinfection, and odor elimination of private parts after washing to alleviate anxiety.

SUMMARY OF THE INVENTION

To solve the above-described problems in the related art, the present invention provides a portable bidet including a cylindrical member having a predetermined length for storing washing liquid, and an airbag section connecting to a rear end portion of the cylindrical member to serve also as a squeeze portion and to supply air to cause injection of washing liquid, wherein the cylindrical member is formed of hard resin and a tip end thereof is formed into an arcuate shape and at least one injection port is provided therein, and the washing liquid is retained therein and an extruding member is disposed therein, the injection port is closed by a film member releasable after storing the washing liquid, the airbag section is formed of flexible or soft resin and has a sealable air inlet, and when not in use, collapsed and packed in a state of being positioned along the side surface of the cylindrical member.

This invention includes additional requirements that the washing liquid is silver ionic water or silver colloid solution of 1-20 ppm in concentration, that the extruding member is a slidable syringe member of a bag member; and that the airbag section is provided with a plug member or a valve member for clogging the air inlet.

According to the portable bidet of the present invention, the washing water is stored in the interior of the cylinder member, the injection port side is closed by the film member, and the airbag section is collapsed and packed in the state of being positioned along the side surface of the cylindrical member when not in use. Therefore, the entire size is formed compact and hence is convenient for carrying. At the same time, when in use, by inflating the airbag section serving also as the squeeze portion, peeling the film member off, and holding and pressurizing the airbag section, the extruding member is moved or deformed so that washing liquid can be spouted out from the injection port. Therefore, not only the operation is very simple, but also sterilization, disinfection, and odor elimination of private parts after washing are achieved and hence anxiety can be alleviated by using silver ion water or silver colloid solution of a required concentration as washing fluid.

DETAILED DESCRIPTION OF THE INVENTION

Subsequently, a concrete embodiment of the present invention will be described in detail based on the drawings.

FIGS. 1 to 4 show a portable bidet according to a first embodiment. The portable bidet generally includes a cylindrical member 1 having a predetermined length for storing washing liquid, and an airbag section 2 connecting to a rear end portion of the cylindrical member and having a function also as a squeeze portion for supplying air to spout the washing liquid.

Figure 1:
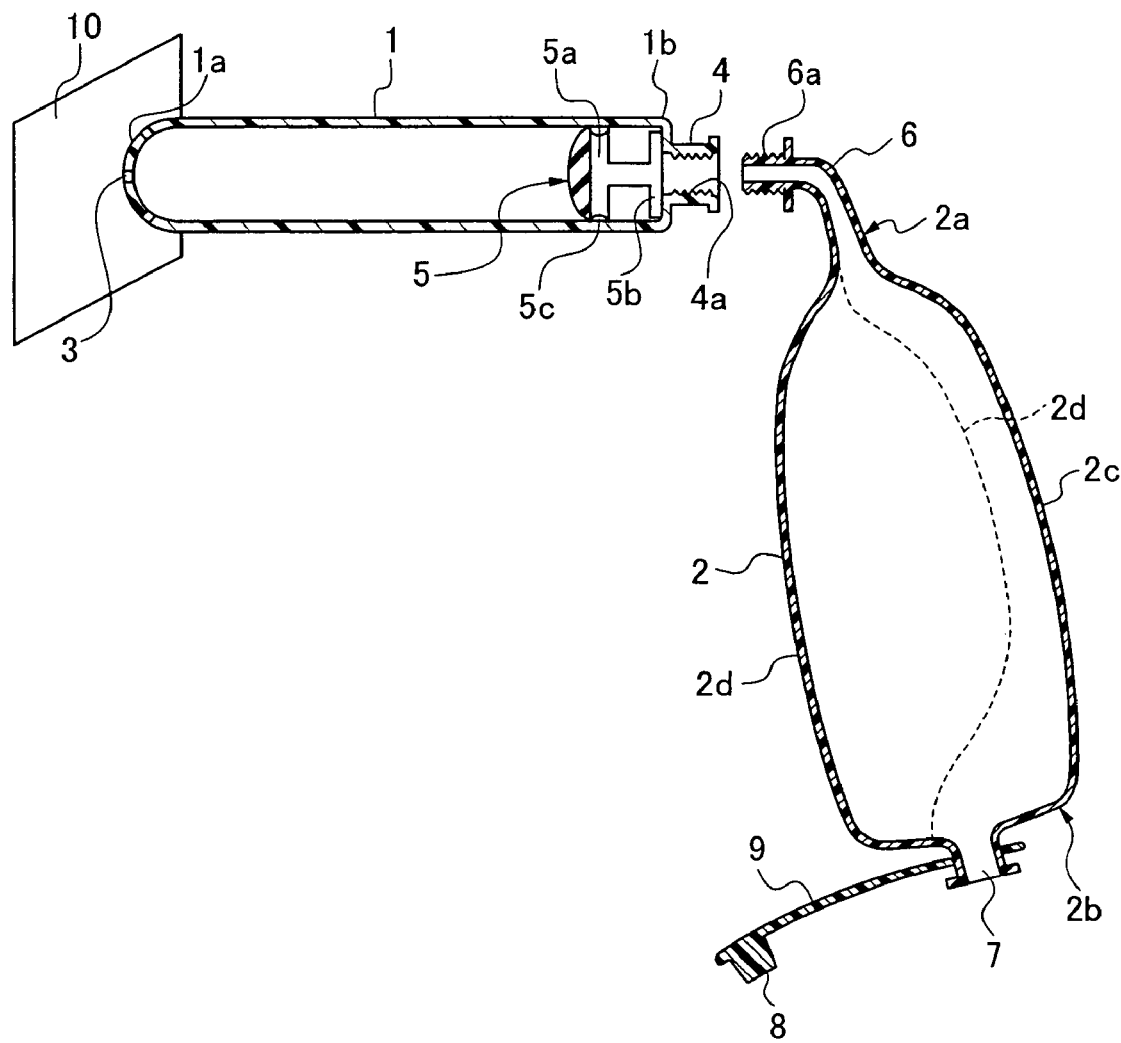
FIG. 1 is a side cross-sectional view showing a principal portion of a portable bidet according to a first embodiment of the present invention in a disassembled state.

The cylindrical member 1 is formed of relatively hard resin material so as to be capable of maintaining the shape and to have a smooth surface. The diameter thereof is substantially between 10 and 20 mm, and the length is substantially between 50 and 100 mm. A tip end portion 1a side thereof is formed into an arcuate shape, and the arcuate tip end is formed with at least one, and preferably, a plurality of three to five injection (ejection) ports 3. The diameter of the injection port 3 is 2 mm or smaller (when one or two ports are provided), and more preferably, 1 mm or smaller (when three to five ports are provided). As shown in FIG. 1, the tip end portion 1a is formed as part of (monolithically with) the cylindrical member 1.

A rear end portion 1b of the cylindrical member 1 is extended with a smaller diameter section 4 for connecting the airbag section 2, and a female screw portion 4a is formed inside the smaller diameter section 4 for connecting the airbag 2. Then, an extruding member 5 is provided inside the rear end portion 1b adjacently to the smaller diameter section 4.

The extruding member 5 in this case is a hand-drum shaped syringe having flange portions 5a, 5b at the front and rear in order to prevent from falling when an air pressure is applied and to reduce friction with respect to the cylinder member 1, and a seal packing 5c is provided at the front flange portion 5a so as to prevent the washing liquid from leaking toward the small diameter section 4 side.

The airbag section 2 is formed of flexible resin having restorability into a capacity as much as about twice the cylindrical member 1, and into substantially a bottle shape or an egg shape. A tip end portion 2a side to be connected with the cylinder member 1 is formed into a smaller diameter section 6 having a predetermined length, and the smaller diameter section 6 is curved in a range substantially between 90 to 120 degrees with a necessary curve radius. The outer surface at the end thereof is formed with a male screw portion 6a to be screwed into the female screw portion 4a. The term, "flexible resin having restorability" used here represents, for example, a tube or a container for mayonnaise or resin of the same type, and the one having moderate hardness and having restorability to a molded shape as long as it is completely bent.

An air inlet 7 is formed so as to project cylindrically at a rear end portion 2b side of the airbag section 2, and a plug member 8 is provided for closing the air inlet 7. In this case, the plug member 8 is attached to an end of a separately formed belt-shaped member 9 of a predetermined length and the other end thereof is attached to the outer peripheral surface of the cylindrically formed air inlet 7, as shown in the drawing. The belt-shaped member 9 may be integrally formed continuously from the opening end portion of the air inlet 7, or may be integrally formed in linear. What is essential is that it can close the air inlet 7 after having introduced air into the airbag section 2, and if there is no plug member 8 provided, it is also possible to adapt to hold with a finger, whereby it can carry out a pumping function by being squeezed and released since it has restorability.

The airbag section 2 may be formed of such resin as not having moderate hardness and restorability as described above. In other words, it must be formed of resin that is relatively flexible in such a manner that the portion from the smaller diameter section 6 to the male screw portion 6a of the airbag section 2 and the portion of the air inlet 7 are formed to be thick, and the other portion may be formed to be relatively thin, for example, it may be extra thin, and formed of resin with less resiliency so that the entire airbag section 2 can be folded to a thin state.

In this case, the capacity of the airbag section 2 may be 2 to 3 times the capacity of the cylindrical member 1, and since the plug member 8 is a necessary member, it is preferable to provide the plug member 8 by integrally forming the belt-shaped member 9 continuously from the edge of the air inlet 7. Since it has no self-restorability, air is introduced from the air inlet 7 to inflate the entirety at the point of use, and the plug member 8 is fitted to the air inlet 7 for use. In any case, it is not necessary to fill the airbag section 2 with air completely, and it is sufficient if air is filled to about 80% of the capacity since the capacity of the airbag section 2 is two to three times the capacity of the cylindrical member 1.

In the first embodiment configured as described above, the tip end portion 1a is oriented upward in a state in which the extruding member 5 is slidably disposed inside the rear end portion 1b of the cylindrical member 1, and the required quantity of washing liquid is filled therein from the tip end portion side with a filling tool, for example, such as a syringe through the injection port 3. Then the filling tool is pulled out, and a film member 10 with an adhesive layer is adhered so as to generally wrap around the tip end portion 1a side to close the injection port 3, whereby the cylindrical member 1 is completely sealed from the outside and in fact serves as a container in which washing liquid is stored. The film member 10 can be peeled off easily from the cylindrical member 1 together with the adhesive layer, and the adhesive layer having no resolvability against the washing liquid is used.

The washing liquid to be injected and filled in the cylindrical member 1 used here is the washing liquid prepared by mixing distilled water with material (including chemicals) having capability of sterilization, disinfection, and odor elimination without causing inflammation on the skin, such as silver ionic water or silver colloid solution of 1 to 20 ppm in concentration.

The airbag section 2 is connected in communication with the rear end portion 1b side of the cylindrical member 1 with the washing liquid filled therein by screwing the male screw portion 6a of the smaller diameter section 6 of the airbag section 2 into the female screw portion 4a of the smaller diameter section 4. When necessary, it is also possible to apply a small quantity of adhesive agent from the outside to completely seal the connection so as to avoid leakage of air from the portion connected with the screw portion.

Figure 2:
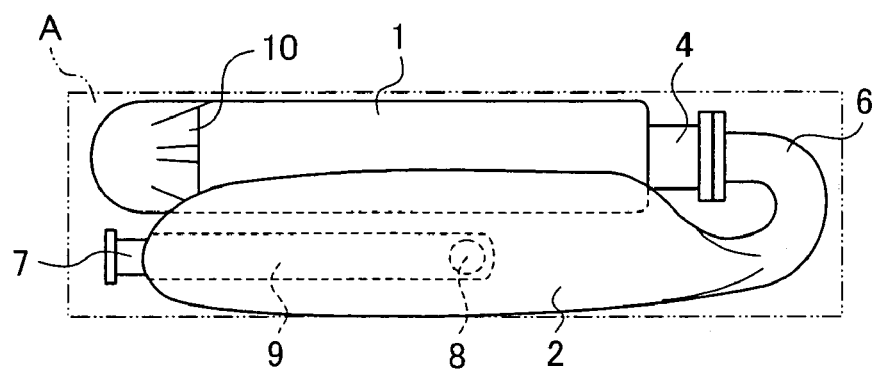
FIG. 2 is a schematic side view showing a packaged state of the portable bidet according to the same embodiment.
Figure 3:
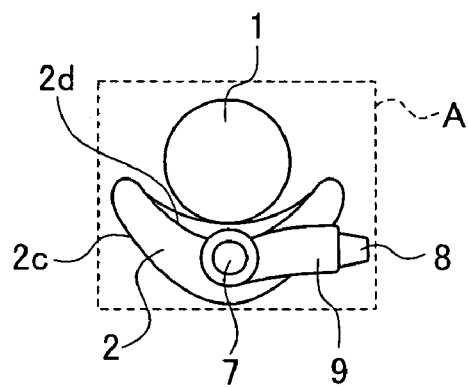
FIG. 3 is a schematic end view showing a packaged state of the portable bidet according to the same embodiment.

In the portable bidet having the airbag section 2 connected to the cylindrical member 1 with the washing liquid stored therein, as shown in FIG. 2 and FIG. 3, air in the airbag section 2 is removed and the entire airbag section 2 is collapsed, a bag side surface 2c on one side is kept as is, a bag side surface 2d on the other side is overlapped so as to be depressed inwardly as shown by an imaginary line (FIG. 1) and the portion of the smaller diameter portion 6 is further curved inwardly, thereby overlapping the cylindrical member 1 and the airbag section 2 in the lengthwise direction, and part of the side surface of the cylindrical member 1 is wrapped by the airbag section 2, whereby the entirety is folded compactly.

In this state, it is placed in a suitable transparent bag member for packaging to keep the compactly folded state, and then it is stored, for example, in a rectangular package box A as shown by an imaginary line to keep up the appearance. Since the entirety is light weight and compactly folded, it is easy to handle, and in particular, not only does it present a good appearance when displayed at the store for sale, but it is also extremely convenient to carry. In the case of the airbag section 2 formed of resin having no hardness and no restorability, it is easier to fold and hence the entirety can be folded further compactly.

When it is actually used, the user takes out the portable bidet from the package box and the bag member for packaging, releases curvature at the section of the smaller diameter section 6, pushes both sides of the airbag section 2 in the overlapped state with fingers to let the bag side surface 2d which is depressed inwardly be pushed outward so that the airbag section 2 is restored into its original bottle shape and hence sufficient quantity of air is taken through the air inlet 7, and then fits the plug member 8 into the air inlet 7 so as to prevent air from leaking.

When the airbag section 2 having no restorability is used, for example, the user puts her mouth to the air inlet 7 to blow air forcedly therein to inflate the airbag section 2, and fits the plug member 8 into the air inlet 7 so as to prevent air from leaking.

Figure 4:
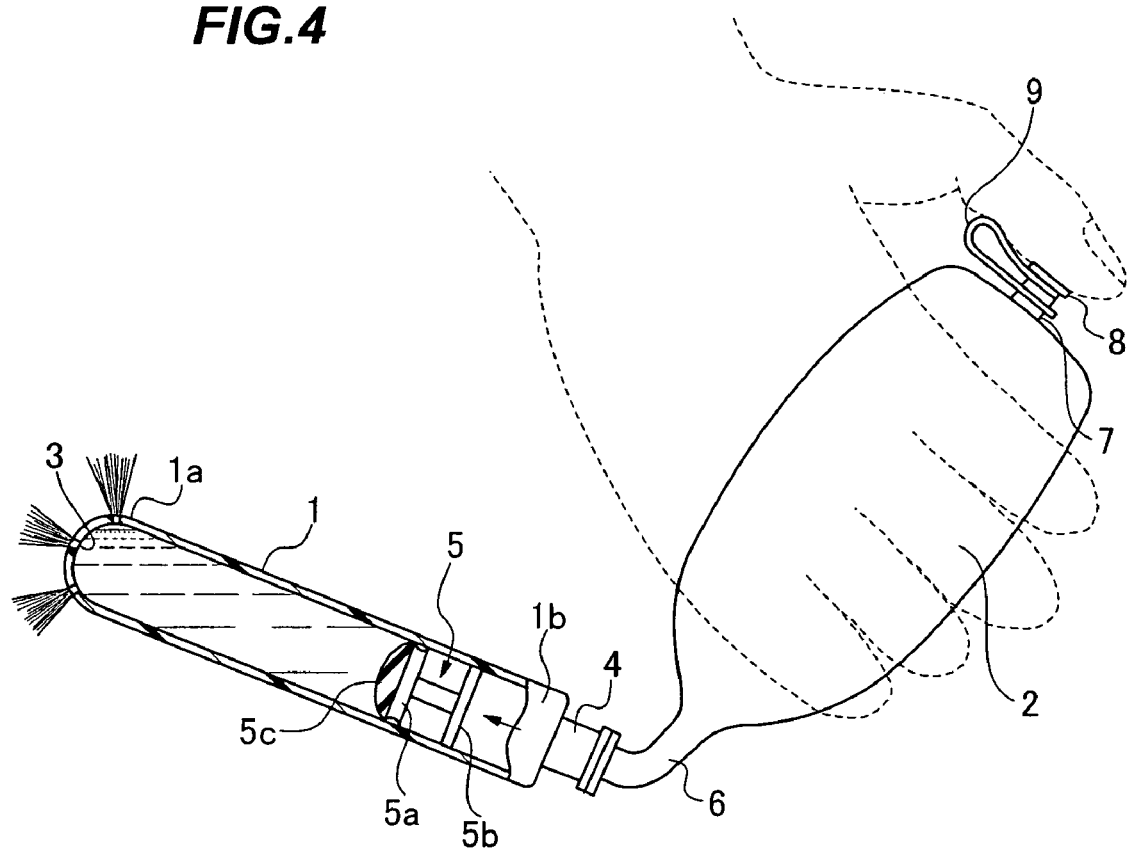
FIG. 4 is a schematic explanatory drawing showing the portable bidet according to the same embodiment in use.

In any case, after having inflated the airbag section 2, by peeling off the film member 10 adhered to the tip end portion 1a of the cylindrical member 1, inserting the cylindrical member 1 into the private part and, as shown in FIG. 4, squeezing the airbag section 2 slowly by hand to supply the compressed air to the cylindrical member 1 side, thereby pushing and moving the extruding member 5 toward the tip end portion 1a side by the supplied compressed air, the washing liquid stored in the cylindrical member 1 is injected or spouted out from the injection port 3 into the private part, whereby washing, sterilization, disinfection, and odor elimination of private parts are achieved.

In this case, since the airbag section 2 has a capacity of about twice or more the capacity of the cylindrical member 1, as long as the air is squeezed out from the airbag section 2 by gripping the airbag section 2 strongly by hand, the extruding member 5 moves continuously and reaches the tip end portion 1a and almost all the washing liquid stored therein can be spouted out. Since the smaller diameter section 6 is hardened by the internal pressure caused by squeezing the airbag section 2, the cylindrical member 1 is prevented from coming out from the private part due to reaction against the spout of the washing liquid even when the user does not hold the cylindrical member 1 as long as the user grips the airbag section 2 firmly, and hence it can be used in the stable state.

Figure 5:
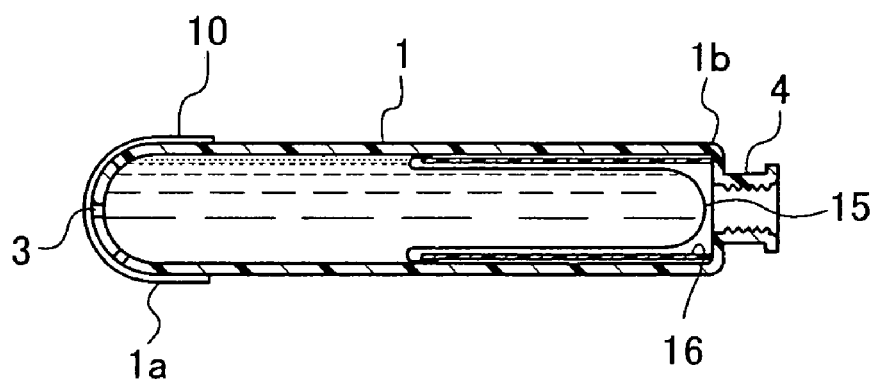
FIG. 5 is a side cross-sectional view of a cylindrical member of the portable bidet according to a second embodiment of the present invention.
Figure 6:
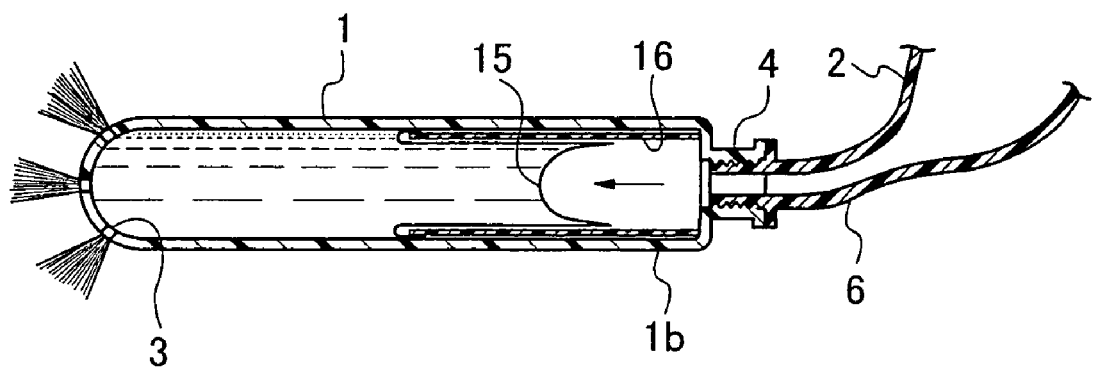
FIG. 6 is a schematic side cross-sectional view of the portable bidet in use according to the second embodiment showing only a principal portion.

FIGS. 5 and 6 show a second embodiment. Since the portable bidet according to the second embodiment is different from the portable bidet according to the first embodiment only in the structure of the extruding member, and other components, that is, the structure of the cylindrical member and the airbag section are substantially the same, they are represented by the same reference numerals and the detailed description will be omitted in order to avoid redundancy.

An extruding member 15 disposed in the cylindrical member 1 is a so-called bag member, and the bag member is formed of pliable thin film material into a shape having the outer diameter which is substantially the same as the inner diameter of the cylindrical member 1 and substantially a half the length of the cylindrical member 1, and an opening of the bag member is fixed to substantially the mid section inside the cylindrical member 1. In this case, for example, attachment is achieved easily by using an inner cylinder 16 having half the length of the cylindrical member 1, mounting the opening of the bag member by clamping tightly between the inner peripheral surface of the cylindrical member 1 and the outer peripheral surface of one end of the inner cylinder 16 so that the inner cylinder 16 is positioned on the rear end portion 1b side.

When the washing liquid is stored in the cylindrical member 1, by filling a required quantity of washing liquid from the injection port 3 on the tip end portion 1a side of the cylindrical member 1, the bag member as the extruding member 15 serves to suspend the washing fluid in a state of being inflated from the midsection toward the rear end portion 1b side of the cylindrical member 1. Therefore, by adhering the separable film member 10 to the tip end portion 1a and sealing the same after the washing liquid is filled and stored therein, the washing liquid is stored and suspended by the cylindrical member 1 and the bag member in a so-called capsulated state.

The structures such that the airbag section 2 is connected in communication with the rear end portion 1b side of the cylindrical member 1 in which the washing liquid is filled, and that the airbag section 2 is collapsed and laid along the cylindrical member 1 and packaged compactly are substantially the same as the structures described in conjunction with the first embodiment.

When using the portable bidet according to the second embodiment, as described in the first embodiment, the user blows air into the airbag section 2 and hence brings into an inflated state, peels the film member 10 on the tip end portion 1a side, inserts the cylindrical member 1 to the private part, and squeezes the airbag section 2 slowly by hand. Accordingly, as shown in FIG. 6, the compressed air is supplied to the cylindrical member 1 side, and the bag member as the extruding member 15 is pressed and deformed toward the tip end portion 1a side by the supplied compressed air, whereby the washing liquid stored in the cylindrical member 1 and the bag member is injected or spouted out from the injection port 3 into the private part, whereby washing, sterilization, disinfection, odor elimination of private parts are achieved.

As long as the user grips the airbag section 2 strongly to let air in the airbag section 2 out, the bag member as the extruding member 15 is continuously deformed by air pressure, and hence a bottom portion of the bag member reaches the tip end portion 1a. Therefore, almost all the washing liquid stored therein can be spouted out, and since the smaller diameter section 6 is hardened by the internal pressure caused by squeezing the airbag section 2, the cylindrical member 1 is prevented from coming out from the private part due to reaction against the spout of the washing liquid even when the user does not hold the cylindrical member 1 as long as the user grips the airbag section 2 firmly, and hence it can be used in the stable state in the same manner as described in the first embodiment.

In any cases, the portable bidet according to the present invention, in brief, includes the cylindrical member 1 for storing the washing liquid, and the airbag section 2 which also serves as the squeeze portion for causing the washing liquid spouted out by air pressure, and the airbag section 2 is folded into a thin state so as not to take up much space for achieving a conveniently portable state for carrying, and when in use, the washing liquid can be spouted out into the private part efficiently by inflating the airbag section 2 and squeezing the same, whereby washing, sterilization, disinfection, and odor elimination of private parts are achieved.

INDUSTRIAL APPLICABILITY

As described above, the portable bidet according to the present invention includes the cylindrical member having a predetermined length for storing the washing liquid and the airbag section connecting to the rear end portion of the cylindrical member to serve also as a squeeze portion and supplying air to cause injection of washing liquid, and the tip end portion thereof is formed into an arcuate shape and at least one injection port is provided therein, the washing liquid is retained therein and an extruding member is disposed therein, and the injection port is closed by a releasable film member after the washing liquid is stored, the airbag section is formed of flexible or soft resin having a sealable air inlet, and when not in use, collapsed and packed in a state in which it is positioned along the side surface of the cylindrical member. Accordingly, not only can the number of parts be reduced to reduce the cost but also the entire size can be formed compact, and that portability can be assured conveniently, and when in use, the airbag section serving also as the squeeze portion is inflated so that the extruding member can be moved or deformed by pressingly grasping the airbag section to spout the washing liquid from the injection port, whereby an operation can be performed very easily.

Also, by using silver ionic water or silver colloid solution of 1 to 20 ppm in concentration as the washing liquid, a superior effect such that it can alleviate anxiety by achieving sterilization, disinfection, and odor elimination of private parts after washing is achieved, being different from the one using tap water.

The invention claimed is:

1. A portable bidet comprising:
   a cylindrical member having a predetermined length for storing washing liquid, said cylindrical member having a front end portion and a rear end portion;
   an airbag section having a sealable air inlet and being fluidically connected to said rear end portion of said cylindrical member;
   wherein said front end portion of said cylindrical member includes a tip end having an arcuate shape and being integrally formed monolithically as part of said cylindrical member;
   wherein said cylindrical member, including said tip end, is formed of hard resin;
   wherein said tip end has at least one ejection port formed therein for ejecting washing liquid therefrom;
   wherein an extruding member is disposed in said cylindrical member to extrude washing liquid from said cylindrical member by ejecting the washing liquid through said at least one ejection port formed in said tip end of said cylindrical member;
   wherein said airbag section is formed of flexible or soft resin so as to be squeezable to force air from said airbag section into said cylindrical member to cause said extruding member to eject washing liquid through said at least one ejection port;
   wherein said cylindrical member and said airbag section are arranged and configured so that said airbag section can be collapsed and packed along a side surface of said cylindrical member in a portable, non-use state; and
   wherein a releasable film is removably provided to close said at least one ejection port so that, once washing liquid has been filled into said cylindrical member, the washing liquid can be retained therein by closing said at least one ejection port with said releasable film and thereby said cylindrical member and said airbag section can be placed in the portable, non-use state with the washing liquid retained in said cylindrical member.

2. A portable bidet according to claim 1, wherein the washing liquid is silver ionic water or silver colloid solution of 1-20 ppm in concentration.

3. A portable bidet according to claim 1, wherein said extruding member is a slidable syringe member or a bag member.

4. A portable bidet according to claim 1, wherein said airbag section is provided with a plug member or a valve member for clogging said air inlet.

* * * * *